(12) United States Patent
Maddern

(10) Patent No.: US 10,579,029 B2
(45) Date of Patent: Mar. 3, 2020

(54) LABORATORY INSTRUMENT CONTROL SYSTEM

(71) Applicant: LEICA BIOSYSTEMS MELBOURNE PTY LTD, Mount Waverly, Victoria (AU)

(72) Inventor: James Maddern, Mont Albert (AU)

(73) Assignee: LEICA BIOSYSTEMS MELBOURNE PTY LTD, Mount Waverly, Victoria (AU)

(*) Notice: Subject to any disclaimer, the term of this patent is extended or adjusted under 35 U.S.C. 154(b) by 0 days.

(21) Appl. No.: 16/054,545

(22) Filed: Aug. 3, 2018

(65) Prior Publication Data

US 2018/0341237 A1 Nov. 29, 2018

Related U.S. Application Data

(63) Continuation of application No. 14/366,814, filed as application No. PCT/AU2012/001606 on Dec. 21, 2012, now Pat. No. 10,054,913.

(60) Provisional application No. 61/579,409, filed on Dec. 22, 2011.

(51) Int. Cl.
| | |
|---|---|
| *G05B 15/02* | (2006.01) |
| *G16H 10/40* | (2018.01) |
| *G16H 40/67* | (2018.01) |
| *H04L 29/06* | (2006.01) |
| *H04L 29/08* | (2006.01) |

(52) U.S. Cl.
CPC ............ *G05B 15/02* (2013.01); *G16H 10/40* (2018.01); *G16H 40/67* (2018.01); *H04L 67/42* (2013.01); *H04L 67/125* (2013.01)

(58) Field of Classification Search
None
See application file for complete search history.

(56) References Cited

U.S. PATENT DOCUMENTS

| | | | |
|---|---|---|---|
| 5,835,384 A | 11/1998 | Lin | |
| 7,010,448 B1 | 3/2006 | Yundt-Pacheco | |
| 7,555,492 B2 | 6/2009 | Herzenberg et al. | |
| 10,054,913 B2* | 8/2018 | Maddern | G05B 15/02 |
| 2004/0093516 A1 | 5/2004 | Hornbeck et al. | |
| 2010/0235896 A1 | 9/2010 | Hirsch | |
| 2011/0208536 A1 | 8/2011 | Luscombe et al. | |
| 2012/0072452 A1 | 3/2012 | Stratman et al. | |

OTHER PUBLICATIONS

International Search Report, PCT/AU2012/001606, dated Feb. 4, 2013.

\* cited by examiner

*Primary Examiner* — Ryan A Jarrett

(74) *Attorney, Agent, or Firm* — Sughrue Mion, PLLC

(57) ABSTRACT

A server computer system connected to a first communications network. The server computer includes an instrument communications component configured to communicate with and control a plurality of biological reagent instruments using the first communications network and a user interface component configured to cause user interface (UI) instances to be displayed by a client computer device connected by a second communications network to said server computer system. The UI instances control respective virtual pods representing one or more of said biological reagent instruments.

17 Claims, 6 Drawing Sheets

LABORATORY INSTRUMENT CONTROL SYSTEM

CROSS REFERENCE TO RELATED APPLICATIONS

This application is a continuation application of U.S. application Ser. No. 14/366,814, filed Jun. 19, 2014, now patent Ser. No. 10/054,913, issue date Aug. 21, 2018, which is a National Stage of International Application No. PCT/AU2012/001606 filed Dec. 21, 2012, claiming the benefit of U.S. Patent Application No. 61/579,409 filed Dec. 22, 2011, the contents of all of which are incorporated herein by reference in their entireties.

TECHNICAL FIELD

The present invention relates to a laboratory instrument control system, and in particular to a network control system for controlling biological reagent instruments.

BACKGROUND

Computer-based control systems have been developed to directly control biological reagent instruments. The instruments are used to automatically apply biological reagents to samples, tissue samples in particular, placed on slides held by the instruments. Instruments of this type are described in International Patent Publications WO 04/001390 and WO 04/08857. A small number of instruments, for example up to five, in one location may be considered to form a "pod", and can be directly controlled by a dedicated computer system.

There are a number of technical problems and limitations associated with existing control systems. For example, the pods are isolated from each other, and there is no communication or data sharing between them. A user of a control system also has to attend a laboratory and the location of the control system and pod to effect control and operate the system. Laboratory Information Systems (LIS's) also are required to be independently connected to the control system of each pod.

It is desired to alleviate one or more difficulties with the prior art, or at least provide a useful alternative.

SUMMARY

Embodiments of the present invention provide a server computer system connected to a first communications network and including:
- an instrument communications component configured to communicate with and control a plurality of biological reagent instruments using the first communications network; and
- a user interface component configured to cause user interface (UI) instances to be displayed by a client computer device connected by a second communications network to said server computer system;
- wherein said UI instances control respective virtual pods representing one or more of said biological reagent instruments.

Embodiments of the present invention further provide a control system including an authentication computer system which allows a user with a client computer device to log on to said authentication computer system using identification data of said user, and to invoke execution of an authentication process to generate credential data for authenticating said client device for a communications session with a server computer system, the communications session enabling the user at the client computer device to control one or more biological reagent instruments in one or more virtual pods.

Embodiments of the present invention further provide a method of generating a user-interface instance for use by a client computer device to control, through a communications network, a virtual pod representing one or more biological reagent instruments, the method including the step of generating and sending to the client computer device the user-interface instance based on user-specific information obtained from identification data of said user, and based one or more virtual pod definitions associated with the user-specific information.

Embodiments of the present invention further provide a method of generating a user-interface (UI) instance for use by a client computer device to control, through a communications network, a virtual pod representing one or more biological reagent instruments, the method including the steps of:
- receiving from the client computer device through the communications network a request for the UI instance;
- generating and sending a first UI instance to the client computer device through the communications network, the first UI instance enabling a user to enter identification data of the user;
- receiving, from a user management component, credential data for authenticating the client computer device;
- retrieving user-specific information from a database component using the credential data, and retrieving from said or another database component one or more virtual pod definitions using the retrieved user-specific information;
- generating and sending to the client computer device the user-interface instance based on the user-specific information and the one or more virtual pod definitions, the user-interface instance enabling a user at the client computer device to control only the virtual pods defined by the virtual pod definitions.

BRIEF DESCRIPTION OF THE DRAWINGS

Some embodiments of the present invention are described herein, by way of example only, with reference to the accompanying drawings, wherein.

DETAILED DESCRIPTION

Figure 1:
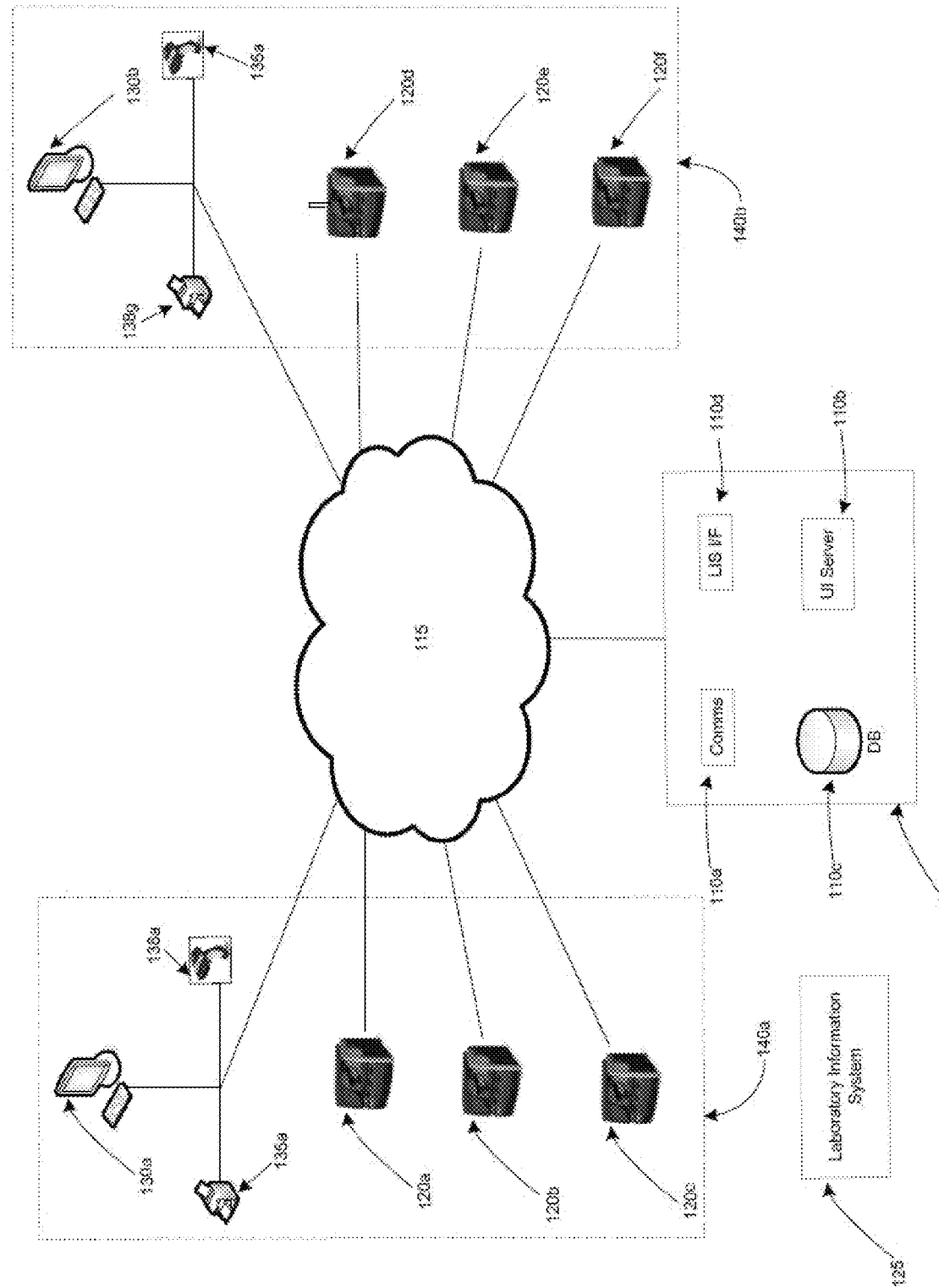
FIG. 1 is an architecture diagram illustrating a communications network connected to a number of peripheral devices.

FIG. 1 illustrates an architecture in which a server computer system 110 is connected, through a communications network 115, to a plurality of biological reagent instruments 120a-120f. The communications network 115 may be a private local area network, a wide area network, the Internet, a virtual private network or any other kind of communications network, and may include either wireless or wired communication links, or both. Also connected to the communications network 115 is a laboratory information system (LIS) 125.

LIS's are information systems maintained and controlled by laboratories that use biological reagent instruments to process tissue and other medical samples. LIS's often store patient data, including diagnostic tests or procedures that may need to be run on samples from specific patients. LIS's are typically off the shelf systems or systems that are customized to the needs of each laboratory.

The biological reagent instruments 120a-120f may be any biological reagent instruments such as advanced staining instruments, autostainers, tissue processors, coverslippers and microarray (DNA, RNA, protein, tissue) instruments, although embodiments of the present invention are particularly suited for use with fully automated instruments, such as the BOND-MAX and Bond III immunohistochemistry and in-situ hybridisation instruments sold by Leica Microsystems, for example. The biological reagent instruments may also include one or more of the various types of biological instruments. For example, the biological reagent instruments of one embodiment of the invention may include a combination of advanced staining instruments and tissue processors. Descriptions of exemplary biological reagent instruments can be found in International Patent Application no. WO 2004/001390 A1 entitled "Biological Reaction Apparatus with Draining Mechanism" and in WO 2009/152569 entitled "Improvements in Staining Instruments and Methods", both in the name of the present applicant, and the descriptions of the biological reagent instruments therein are hereby expressly incorporated herein by reference.

The biological reagent instruments 120a-120f may be located in any site to which a computer network connection such as, but not limited to, an internet connection, data transfer connection, wired or wireless connection may be achieved. The biological reagent instruments 120a-120f may be located in the same or different geographic locations; for example, different areas of a single laboratory, or in different laboratories located at the same or at different sites. It may be useful to have biological reagent instruments 120a-120f spatially co-located in groups, such that a single operator has easy simultaneous physical access to a group of instruments 120a-120f.

Each of the biological reagent instruments 120a-120f is controlled by the server computer system 110, and more specifically, an instrument communications component 110a of the server computer system 110. The instrument communications component 110a sends instructions through the communications network 115 to the biological reagent instruments 120a-120f, and receives messages (including status messages) from biological reagent instruments 120a-120f. Server computer system 110 can be of any configuration, including, for example, a single computer having at least one CPU, or multiple distributed multi-CPU machines acting in concert. The instrument communications component 110a may be a software application, a configurable hardware component such as a Field Programmable Gate Array (FPGA), or a dedicated hardware component such as an Application Specific Integrated Circuit (ASIC) or any combination of these.

The server computer system 110 also includes a user interface component 110b. The user interface component 110b generates and sends user interface (UI) instances to one or more client computer devices connected to the server computer system 110 by a communications link or network. The communications link or network may be the same network 115 by which the server computer system 110 communications with biological reagent instruments 120a-120f (communications network 115), or may be a different communications link or network. FIG. 1 shows, as an example, two client computer devices 130a and 130b. Each UI instance is displayed on one or more display devices (e.g. video display units, monitors etc) (not shown) associated with a client computer device (130a, 130b). This enables a user at either client computer device 130a, 130b to interact with the corresponding UI instance, and therefore to interact with the server computer system 110, to send instructions to, and receive messages from, the one or more biological reagent instruments 120a-120f.

The user interface component 110b may generate and send the user interface instances indirectly by generating and sending to the one or more client computer devices 130a, 130b instructions for launching or generating the user interface instances. Alternatively, user interface component 110b may generate and send user interface instances by generating and sending to the one or more client computer devices 130, 130b instructions for client software already installed at the one or more client computer devices (including, for example, instructions to the client software to launch a user interface instance).

The server computer system 110 may also be at any location, as long as it is connected, via one or more communications networks, to client computer devices 130, 130b and biological reagent instruments 120a-120f.

Each UI instance controls a respective virtual pod. A virtual pod represents one or more of the biological reagent instruments 120a-120f. FIG. 1 shows the biological reagent instruments 120a-120f divided into two virtual pods, with biological reagent instruments 120a, 120b and 120c grouped into a first virtual pod 140a, and biological reagent instruments 120d, 120e and 120f grouped into a second virtual pod 140b. The UI instance invoked and sent by the clinical user interface 110b to client computer device 130a is used to control the first virtual pod 140a. Similarly, the UI instance invoked and sent by the clinical user interface 110b to client computer device 130b is used to control the second virtual pod 140b. In a general sense, the size of the virtual pod may be of an unlimited scale. However, in practice the size of a virtual pod is usually based on the physical space available at each site, or by the number of biological reagent instruments that are desired to be controlled by a single user or client computer device.

In one embodiment, a virtual pod may include more than 500 biological reagent instruments. In a further embodiment, a virtual pod may include from 250 to 500 biological reagent instruments. In one embodiment, a virtual pod may include from 100 to 250 biological reagent instruments. In a further embodiment, a virtual pod may include from 20 to 100 biological reagent instruments. In a further embodiment, a virtual pod may include 6 to 20 biological reagent instruments. In a further embodiment, a virtual pod may include from 1 to 5 biological reagent instruments.

The biological reagent instruments 120a-120f may be grouped into virtual pods on the basis of any criterion or criteria. In some embodiments, commonly configured biological reagent instruments are grouped together in a virtual pod. For example, biological reagent instruments 120a, 120b and 120c may be configured exclusively to undertake research activities, virtual pod 140a becoming a "research pod". Similarly, biological reagent instruments 120d, 120e and 120f may form a "clinical pod" 140b, each of the instruments 120d, 120e and 120f being configured to exclusively undertake clinical activities. This means that client computer system 130a controls, by means of the server computer system 110, the research pod 140a, while client computer system 130b controls, again by means of the server computer system 110, the clinical pod 140b. All of the members of the clinical pod 140b (namely biological reagent instruments 120d, 120e and 120f) may be configured to use only a predetermined set of procedures, being those procedures suitable for clinical activities. Similarly, the research pod biological reagent instruments 120a, 120b and 120c may be configured to use a predetermined set of reagents, some of which may be suitable for research use but have not yet been sufficiently tested for clinical use, and a predetermined set of procedures (again, some of which may not be suitable for clinical use).

As one example, twenty biological reagent instruments may be grouped into two virtual pods. A first virtual pod may contain nine biological reagent instruments used to assist with clinical diagnosis. The second virtual pod may contain eleven biological reagent instruments, used for research only. The biological reagent instruments in the first virtual pod may be configured to only run protocols or procedures that have been approved by an independent third party.

In another example, twenty-five biological instruments may be grouped into three virtual pods. The first virtual pod may be for test protocols and procedures, and the six biological instruments in this pod may be configured to use experimental procedures, possibly with experimental reagents. The second virtual pod may consist of ten biological reagent instruments used for clinical diagnosis. The third virtual pod, consisting of nine biological reagent instruments, may be used for research purposes only.

In a further example, a virtual pod of five instruments may consist of three instruments that are used for clinical diagnosis, and two instruments used for research purposes.

As indicated above, virtual pods may be of any size, and may consist of biological reagent instruments that are similarly configured, or alternatively may consist of biological reagent instruments that are otherwise related (for example, instruments in the same geographic location). Alternatively, the virtual pods may consist of biological reagent instruments that are not similarly configured or located in the same geographic location.

In addition to controlling a virtual pod representing a group of biological reagent instruments, the UI instance invoked and sent by the user interface component 110b to the client computer device (130a, 130b) may control one or more peripheral devices. For example, the biological reagent instruments of the research pod 140a (120a, 120b and 120c) may be commonly configured to use a common set of peripheral devices such, for example, a label printer 135a, standard printer, barcode scanner/reader 138a, RFID scanner/reader, biometric scanner/reader, and other digital imaging devices. The peripheral devices, such as the label printer 135a and barcode scanner 138a may be directly connected to the server computer system 110 through the communications network 115. Alternatively, the peripheral devices may be connected directly to the client computer device 130a. Regardless of how the peripheral devices are connected, they are associated exclusively or non-exclusively with a corresponding virtual pod.

Figure 2:
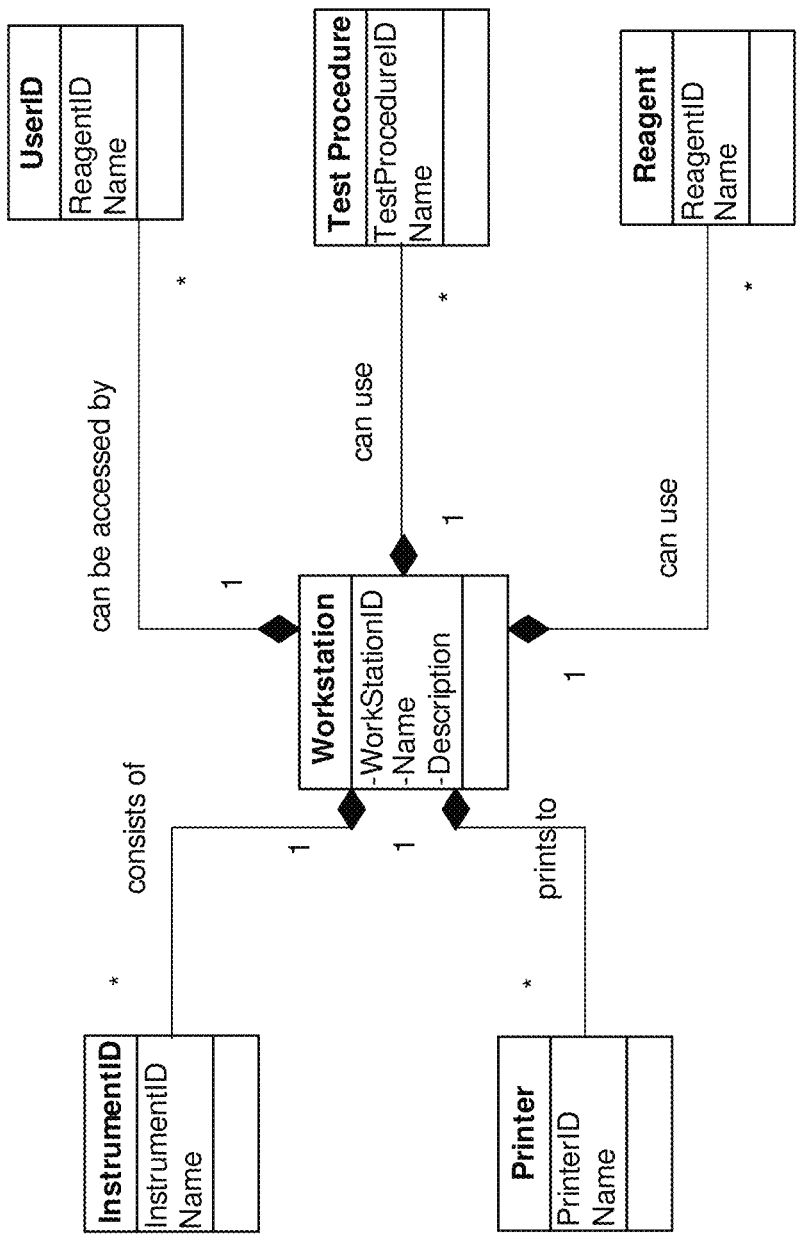
FIG. 2 is a data schema for virtual pod definition data.

The virtual pods 140a, 140b are defined by pod definition data, which is stored in a database component 110c of the server computer system 110. Pod definition data includes data identifying the specific biological reagent instruments 120a-120f that are part of the pod. Pod definition data may also include data identifying the peripheral devices for which the biological reagent instruments in the pod are configured. The pod definition data may be modified by a user to reconfigure the membership and existence of virtual pods. This allows for dynamic grouping of biological reagent instruments 120a-120f, and virtual pod membership may be altered without reconfiguring any part of the biological reagent instruments 120a-120f themselves. An example of a database schema for the pod definition data is shown in FIG. 2.

The user interface component 110b may request pod definition data from the database component 110c. This enables the user interface component 110b to include information about virtual pod membership in the one or more UI instances it generates. It also enables the user interface component 110b to bind specific UI instances to specific pods, which is done if a single specific UI instance is to control only a single corresponding virtual pod, or is to control a predetermined number of virtual pods.

To enable the execution of appropriate sample processing protocols, as described above the server computer system 110 is connected to LIS 125 through the communication network 115. The server computer system 110 includes an LIS interface component 110d that enables the server computer system 110 to receive information from the LIS 125, thereby enabling the server computer system 110 to control the biological reagent instruments 120a-120f in accordance with appropriate protocols. The LIS 125 may store patient data and the names of tests required to be applied to patient samples. In some configurations, it may store additional data, including protocol-related data.

Figure 3:
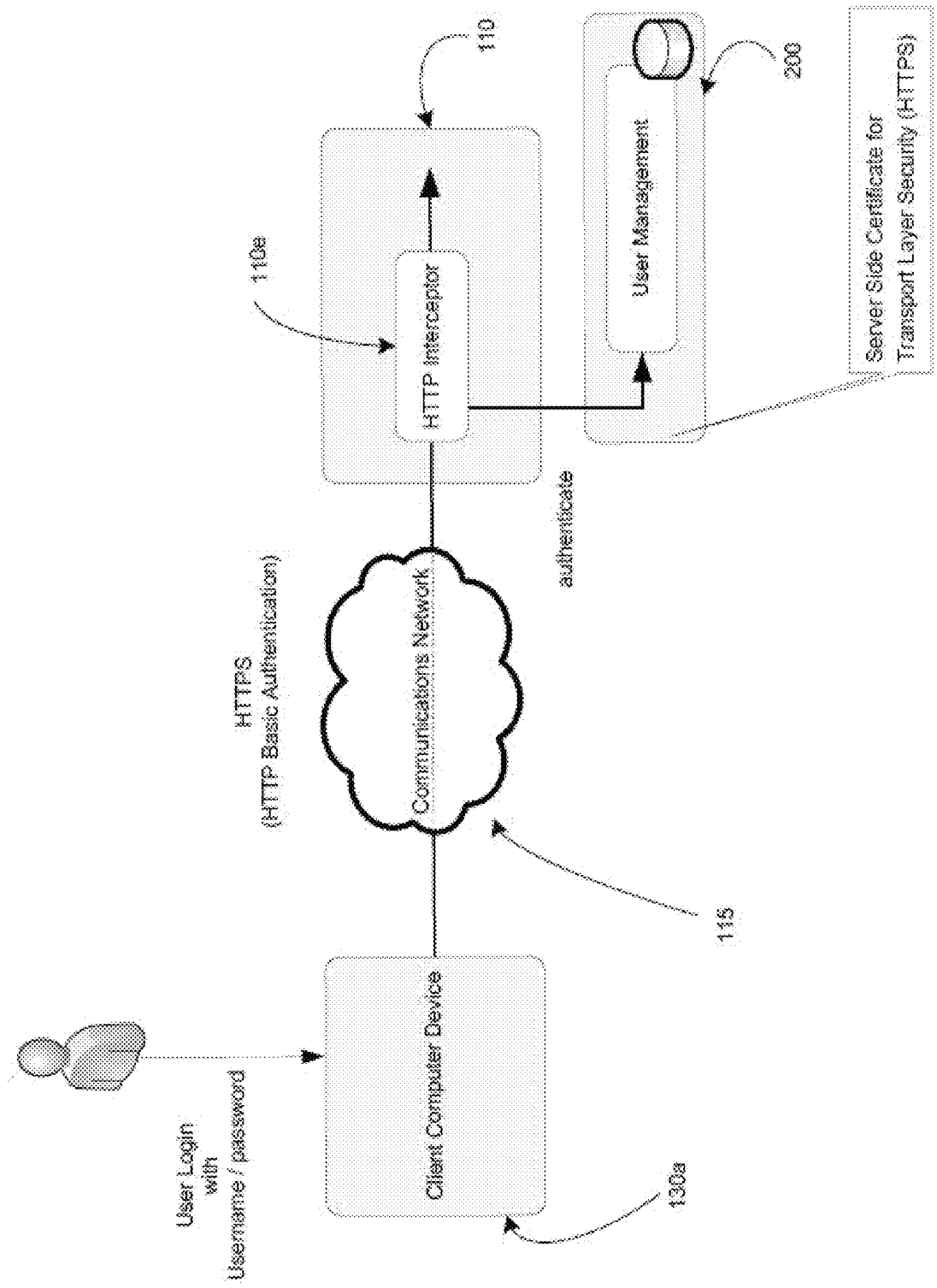
FIG. 3 is an architecture diagram illustrating a client device connected to an authentication computer system.

Users at client computer devices 130a and 130b may be required to be authenticated in order to control any of the virtual pods 140a, 140b. The user may enter their username and password (or other identification data) into the UI instance at the client computer device 130a, 130b. This identification data is sent to an authentication computer system. This authentication computer system may be in the form of a user management component 200, as illustrated in FIG. 3. User management component 200 may be a component within server computer system 110. Alternatively, it may be or be part of a distinct computer system. In the latter case, the server computer system 110 may include an interception component 110e for intercepting any identification data sent to the server computer system 110 from a client computer device 130a, 130b, and redirecting (or resending) that identification data to the user management component 200. Alternatively, client computer devices 130a, 130b may be configured to send identification data directly to the user management component 200, for example where the user management component 200 is a computer system distinct from the server computer system 110.

Where the UI instances are displayed on the client computer device 130a, 130b by a web browser application, the identification data may be sent using HTTP Basic authentication, during a HTTPS session. Other forms of identification data and authentication mechanisms may be used. For example, Digest authentication or Form-Based authentication may be used instead of Basic authentication, again preferably over an HTTPS session.

The authentication computer system may be an existing system that at least in part operates independently of the server computer system 110, such as an Active Directory authentication system, or an authentication system that uses LDAP lookups. Such systems may already be operational and in place at the laboratory, and may be reconfigured to operate as described above.

Upon receipt of the identification data, the user management component 200 invokes the execution of an authentication process to generate credential data for authenticating the client computer device for a communications session with the server computer system 110, the communications session enabling a user at the client computer device to control one or more biological reagent instruments in one or more virtual pods. The credential data is sent to the server computer system 110.

By having a separate authentication computer system (user management component 200) undertake the task of user authentication, authentication and user details need not be stored in the server computer system 110 (where the authentication computer system 200 is distinct from the server computer system 110), or may be compartmentalised in a separate component (where the authentication computer system is a sub-system of computer system 110).

In one embodiment, the user interface component 110b is a web server, such as the Apache HTTP Server, which may execute scripts (such as those written in PHP), and can read to or write from database storage using an appropriate language, such as SQL. In such an embodiment, the user interface component receives HTTP requests including user credentials in the HTTP Authentication header. These requests are redirected to, and authenticated by, the authentication computer system 200 before the HTTP requests are passed on to the server computer system 110.

Where the user interface component 110b is a web server, the UI instances may be rendered at the client computer device 130a, 130b using a standard web browser application. The user interface instances may take the form of a markup language such as HTML or XML, together with scripts such as those written in PHP or JavaScript. Alternatively, a suitable application framework, such as Microsoft Silverlight or Adobe Flash may be used.

As described above, in other embodiments the user interface component 110b may not be a web server, and may be a UI server which modifies the behaviour or appearance of user interface instances created by software executing on the client computer devices 130a, 130b.

Figure 4:
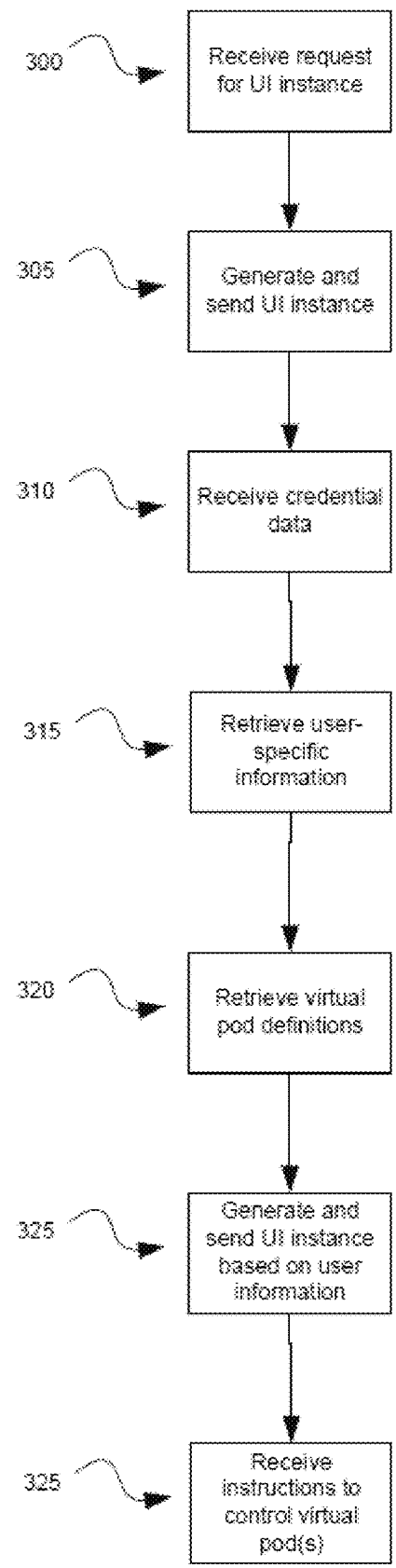
FIG. 4 illustrates a process that may be undertaken by a server computer system to generate a user-interface instance for use by a client computer device.

FIG. 4 illustrates a process that may be undertaken by server computer system 110 to generate a user-interface instance for use by a client computer device (for example, client computer device 130a) to control, through a communications network 115, a virtual pod 140a, 140b representing one or more biological reagent instruments 120a-120f. At step 300, the server computer system 110 receives from the client computer device 130a a request for the UI instance. The client computer device 130a may generate this request automatically upon booting up of the client computer device 130a. Alternatively, the request may be generated upon the launch of a dedicated application, or a standard web browser application, on client computer device 130a. In response to the request, at step 305, the server computer system 110 generates and sends a first UI instance to the client computer device 130a through communications network 115. This may involve the server computer 110 sending instructions to the client computer device 130a to launch a first UI instance generated at the client computer device 130a. The first UI instance prompts the user to enter identification data unique to the user (for example, a username and password). As discussed above, this identification data is sent to an authentication computer system 200 (either directly, or through a redirection).

The server computer system 110 receives from the user management component 200, at step 310, credential data for authenticating the client computer device 130a. The authentication of the client computer device 130a is a substitute for authenticating the user directly, the authentication enabling the client computer device 130a, on instructions from the user, to control one or more biological reagent instruments 120a-120f in a virtual pod.

Each user of the server computer system 110 is associated with one or more roles. Each role is associated with rule data that identifies the actions that are allowed to be performed by users having that role, and the results data visible to users having the role. The server computer system 110 retrieves the user-specific information (for example, role information) from a database component (for example, database 110c, or another database) (step 315). The server computer system 110 also retrieves from the database (for example, database 110c), at step 320, virtual pod definitions (in the form of pod definition data) using the user-specific information. The virtual pod definitions that are retrieved are only those definitions for virtual pods associated with a specific user (or a specific role associated with the user).

Figure 5:
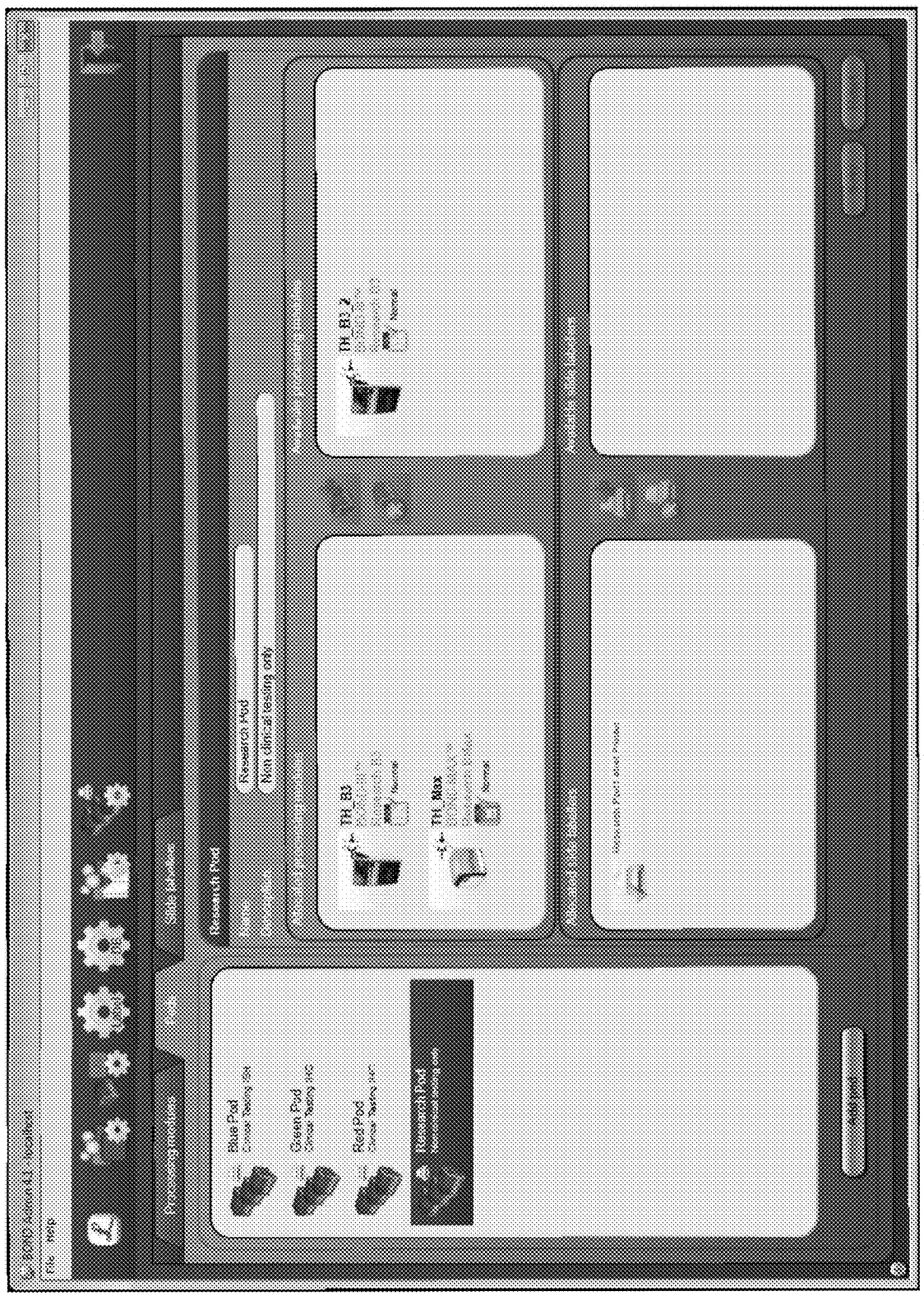
FIG. 5 is an illustration of an exemplary user interface.

At step 325, the user interface component 110b of the server computer system 110 generates and sends to the client computer device 130a the user-interface instance based on the user-specific information and the one or more virtual pod definitions, the user-interface instance enabling a user at the client computer device 130a to control only the virtual pods defined by the (retrieved) virtual pod definitions. The user interface component 110b tailors the user interface instance by only showing (or enabling the activation of) user interface elements for actions that the user is able to take (based on the user or the role definitions associated with the user), and only showing information relating to virtual pods that the user has the authority to control. An example screenshot of a user interface, showing the virtual pods that the user has the authority to control, is shown in FIG. 5. Preferably, the user interface shows only, for each virtual pod over which the user has control:

the instruments allocated to that virtual pod;
the cases and slides that are being processed on that virtual pod;
the maintenance schedule for the instruments in that virtual pod;
the test procedures and reagents that are allowed to be used on that virtual pod.

Figure 6:
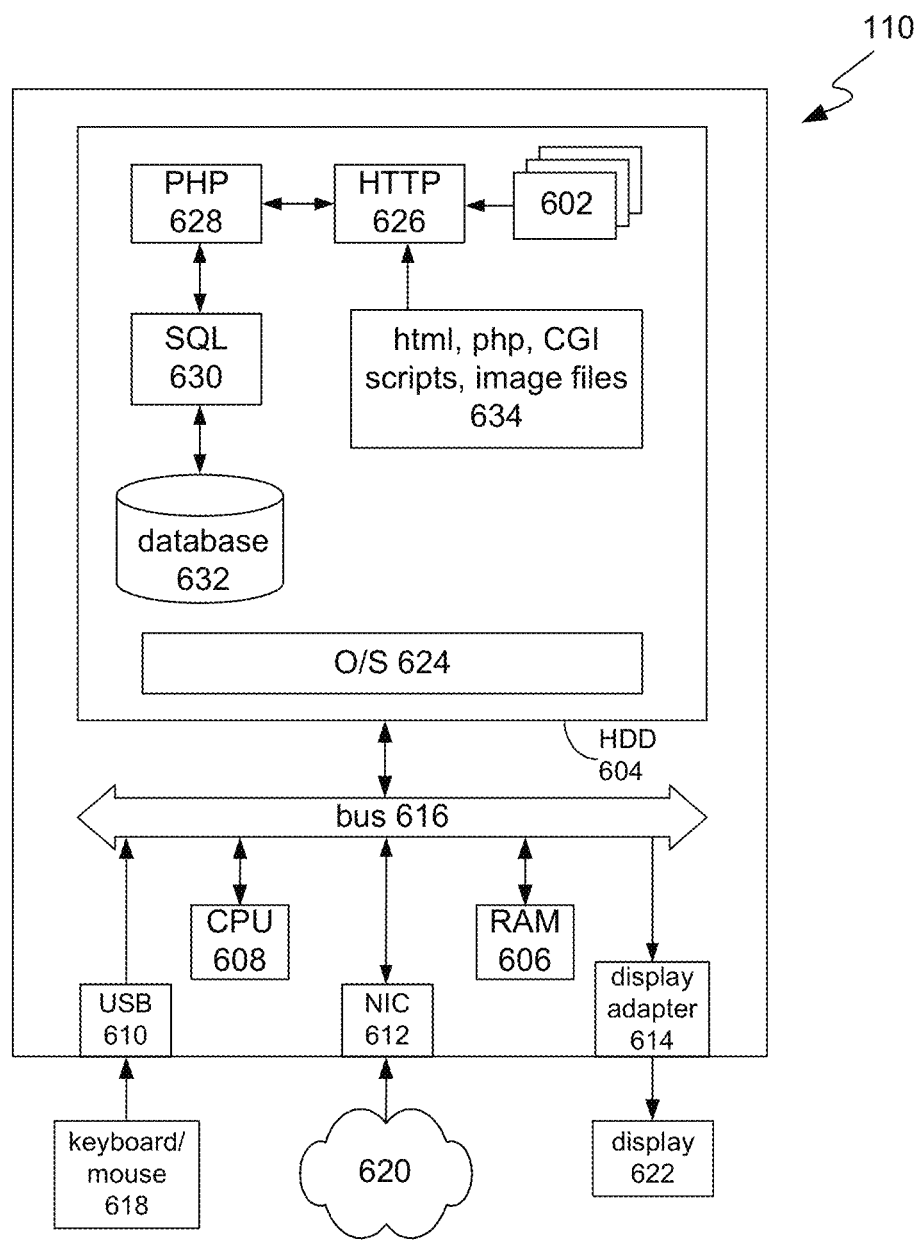
FIG. 6 is an illustration of an exemplary architecture of a server computer system configured to generate a user-interface instance for use by a client computer device.

In the described embodiment, the server computer system 110 is a standard computer system such as an 32-bit or 64-bit Intel Architecture based computer system, as shown in FIG. 6, and the process described above with reference to FIG. 4 executed by the server computer system 110 is implemented in the form of programming instructions of one or more software modules 602 stored on non-volatile (e.g., hard disk) storage 604 associated with the computer system, as shown in FIG. 6. However, it will be apparent that at least parts of the process described above with reference to FIG. 4 could alternatively be implemented as one or more dedicated hardware components, such as application-specific integrated circuits (ASICs) and/or field programmable gate arrays (FPGAs).

The server computer system 110 includes standard computer components, including random access memory (RAM) 606, at least one processor 608, and external interfaces 610, 612, 614, all interconnected by a bus 616. The external interfaces include universal serial bus (USB) interfaces 610, at least one of which is connected to a keyboard and a pointing device such as a mouse 618, a network interface connector (NIC) 612 which connects the system 110 to a communications network 115, and a display adapter 614, which is connected to a display device such as an LCD panel display 622.

The system 110 also includes a number of standard software modules 626 to 630, including an operating system 624 such as Linux or Microsoft Windows, web server software 626 such as Apache, available at http://www.apache.org, scripting language support 628 such as PHP, available at http://www.php.net, or Microsoft ASP, and structured query language (SQL) support 630 such as MySQL, available from http://www.mysql.com, which allows data to be stored in and retrieved from an SQL database 632.

Together, the web server 626, scripting language 628, and SQL modules 630 provide the system 110 with the general ability to allow client computing devices 130a, 130b equipped with standard web browser software to access the system 110 and in particular to provide data to and receive data from the database 632.

However, it will be understood by those skilled in the art that the specific functionality provided by the system 110 to such users is provided by scripts accessible by the web server 626, including the one or more software modules 602 implementing the process described above with reference to FIG. 4, and also any other scripts and supporting data 634, including markup language (e.g., HTML, XML) scripts, PHP (or ASP), and/or CGI scripts, image files, style sheets, and the like.

The use of virtual pods, as described above, has at least the following advantages:
  laboratory users can easily configure and reconfigure groups of laboratory reagent instruments and associated peripheral devices without having to physically re-connect or rewire instruments or peripheral devices;
  instruments and peripheral devices may be physically moved without the need for any reconfiguration;
  users can be assigned pods having instruments configured appropriately to their role and/or experience;
  users are presented with a user interface uncluttered by instruments and functions to which they do not have access;
  reagents can be restricted to specific instruments; for example reagents for research purposes can be restricted to research only instruments (that may form a research-only virtual pod); or tests approved by government agencies (such as the United States Food and Drug Administration) may only run on certified instruments or instruments listed in the government registration for that particular test; and
  tests can be allocated (and confined) to instruments which have been the subject of regulatory approval.

Many modifications will be apparent to those skilled in the art without parting from the scope of the present invention.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

What is claimed is:

1. A server computer system comprising:
  a processor configured to control communication with and control at least two virtual pods which comprise a first virtual pod and a second virtual pod, wherein the first virtual pod comprises a first set of at least two biological reagent instruments from among a plurality of biological reagent instruments and a first dedicated user interface (UI) instance, to be displayed by a client computer device, wherein the first dedicated UI instance controls said at least two of the plurality of biological reagent instruments and the second virtual pod comprises a second set of at least two other biological reagent instruments from among the plurality of biological reagent instruments and a second dedicated UI instance, to be displayed by the client computer device, wherein the second dedicated UI instance controls the second set of the at least two other biological reagent instruments,
  wherein the processor is further configured to control communication with the plurality of biological reagent instruments using a first communications network, and to control communication with the client computer to provide the first dedicated UI instance and the second dedicated UI instance via a second communications network,
  wherein, in response to a request, from the client computer device, to control the first virtual pod, the processor controls to communicate the first UI instance to the client computer device so that the first set of biological reagent instruments are controlled by the client computer device using the received first UI instance, wherein the client computer device is remote from the first virtual pod, and
  wherein the first virtual pod is at a physical location different from a location of the second virtual pod.

2. The server computer system as claimed in claim 1, wherein the first set of the at least two biological reagent instruments are commonly configured to undertake a first type of activities and wherein the second set of the at least two other biological reagent instruments are commonly configured to undertake a second type of activities different from the first type of activities.

3. The server computer system as claimed in claim 2, wherein the first dedicated UI instance controls all of the biological reagent instruments in the first virtual pod and peripheral devices dedicated to the first virtual pod and the second dedicated UI instance controls all of the biological reagent instruments in the second virtual pod and the peripheral devices dedicated to the second virtual pod.

4. The server computer system as claimed in claim 1, wherein the first set of the at least two biological reagent instruments of the first virtual pod are commonly configured to exclusively perform at least one specific task or type of task and wherein the second set of the at least two other biological reagent instructions of the second virtual pod are commonly configured to exclusively perform the same at least one specific task or the type of task.

5. The server computer system as claimed in claim 1, wherein the first set of the at least two biological reagent instruments of the first virtual pod are commonly configured to use:
  a predetermined set of reagents; and
  a predetermined set of procedures, and
  wherein the first dedicated UI instance, generated by the processor, comprises instructions to control the at least two biological reagent instruments to interact with the predetermined set of reagents and to execute the predetermined set of procedures.

6. The server computer system as claimed in claim 1, wherein the first set of the at least two biological reagent instruments of the first virtual pod are commonly configured to use a first common set of peripheral devices and wherein the second set of the at least two other biological reagent instruments of the second virtual pod are commonly configured to use a second common set of peripheral devices located at a physical location different from the first common set of peripheral devices.

7. The server computer system as claimed in claim 6, wherein at least one of the first common set of peripheral devices and the second common set of peripheral devices comprises at least one of: a label printer; and a barcode scanner.

8. The server computer system as claimed in claim 1, further comprising a memory configured to store pod definition data representing one or more virtual pod definitions of the first virtual pod and the second virtual pod and wherein the processor obtains from the memory the pod definition data to generate the plurality of UI instances.

9. The server computer system as claimed in claim 1, further comprising a transceiver component configured to communicate with a laboratory information system via the first communication network,
wherein the processor is further configured to interface with, and receive, via the transceiver, laboratory information from a laboratory information system.

10. The server computer system as claimed in claim 9, wherein the processor receives laboratory information relating to at least one of the configuration and operation of at least one of the virtual pods.

11. The server computer system as claimed in claim 1, wherein the processor is further configured to receive credential data for authenticating a user of the client computer device, and to retrieve user-specific information from a memory, wherein the processor is further configured to customize the UI instances based on the user-specific information.

12. The server computer system as claimed in claim 1, further comprising a transceiver configured to communicate with the client computer device via the first communication network, wherein the processor is further configured to generate and send, via the transceiver, UI instances to be rendered at the client computer device using a web browser.

13. The server computer system as claimed in claim 1, wherein each of the first dedicated UI instance and the second dedicated UI instance comprises instructions for the client computer device to launch, or modify the behavior or appearance of, a user interface generated at the client computer device.

14. The server computer system as claimed in claim 1, wherein the biological reagent instruments comprise at least three of a staining instrument, autostainer, tissue processor, coverslippers, and microarray instruments and wherein the first virtual pod is at a first laboratory and the second virtual pod at a second laboratory, which is remote from the first laboratory.

15. The server computer system as claimed in claim 1, wherein each of the first dedicated UI instance and the second dedicated UI instance is in a markup language and comprises software instructions to control the at least two biological reagent instruments of the first virtual pod, cases, and slides processed by the at least two biological reagent instruments, maintenance schedule of the at least two biological reagent instruments, and test procedures and reagents that are used by the respective virtual pod.

16. A method of controlling a plurality of biological reagent instruments, the method comprising:
receiving, by a server from a first client computer which is a dedicated computer for a first virtual pod from among a plurality of virtual pods, a request to control a second virtual pod from among the plurality of virtual pods, wherein each of the plurality of virtual pods comprises an exclusive set of at least two from among the plurality of biological reagent instruments;
in response to receiving the request, the server generates a plurality of user interface (UI) instances for the plurality of virtual pods comprising a first UI instance comprising a first set of instructions to control the first virtual pod including instructions to control the respective set of the at least two biological reagent instruments belonging to the first virtual pod and a second user interface (UI) instance which comprises instructions to control the second virtual pod including instructions to control the respective set of the at least two biological reagent instruments belonging to the second virtual pod; and
transmitting, from the server, the generated second UI instance to the first client computer which controls the second virtual pod via the server using the second UI instance,
wherein the first client computer controls the first virtual pod and the second virtual pod via the server, and
wherein the first client computer is remote from the first virtual pod.

17. The method of claim 16, wherein the first virtual pod and the second virtual pod are configured to perform different types of tasks, and
wherein the generating, by the server, of the plurality of UI instances comprises:
retrieving, from a memory pod, data definitions which comprises data identifying each of the plurality of biological reagent instruments and classifying the respective biological reagent instrument to one of the plurality of virtual pods and data identifying peripheral devices belonging to the respective virtual pod from among the plurality of virtual pods; and
generating the plurality of the UI instances based on the retrieved pod data definitions such that each of the plurality of the UI instances comprises the instructions dedicated to control only the biological reagent instruments and the peripheral devices belonging to the respective virtual pod.

* * * * *